United States Patent
Chow et al.

(10) Patent No.: US 9,059,408 B2
(45) Date of Patent: Jun. 16, 2015

(54) HEXACENE DERIVATIVE, METHOD FOR FORMING HEXACENE, METHOD FOR FORMING HEXACENE CRYSTAL, PROCESS FOR MAKING ORGANIC SEMICONDUCTOR DEVICE, AND ORGANIC SEMICONDUCTOR DEVICE

(71) Applicant: Academia Sinica, Taipei (TW)

(72) Inventors: Ta-Hsin Chow, Taipei County (TW); Motonori Watanabe, New Taipei (TW); Yuan Jay Chang, Taipei (TW); Yu-Tai Tao, Taipei (TW); Ting-Han Chao, Taipei (TW); Shun-Wei Liu, Taoyuan County (TW); Chih-Hsien Yuan, Taipei (TW); Teruo Shinmyozu, Koga (JP); Kenta Goto, Fukuoka (JP); Md.Minarul Islam, Dhaka (BD)

(73) Assignee: Academia Sinica, Taipei (TW)

( * ) Notice: Subject to any disclaimer, the term of this patent is extended or adjusted under 35 U.S.C. 154(b) by 292 days.

(21) Appl. No.: 13/668,334

(22) Filed: Nov. 5, 2012

(65) Prior Publication Data

US 2014/0124740 A1 May 8, 2014

(51) Int. Cl.
| H01B 1/12 | (2006.01) |
| C07C 15/00 | (2006.01) |
| C07C 15/20 | (2006.01) |
| H01L 51/00 | (2006.01) |
| C07C 1/207 | (2006.01) |
| H01L 51/05 | (2006.01) |

(52) U.S. Cl.
CPC ........ *H01L 51/0026* (2013.01); *H01L 51/0056* (2013.01); *H01L 51/0558* (2013.01); *C07C 1/2076* (2013.01); *C07C 2103/54* (2013.01)

(58) Field of Classification Search
CPC ... H01B 1/12; C08L 2201/04; H01L 51/0056; C07C 15/00; C07C 15/20
See application file for complete search history.

(56) References Cited

U.S. PATENT DOCUMENTS

2009/0226634 A1  9/2009 Chow et al.

OTHER PUBLICATIONS

Watanabe et al., "The Synthesis, Crystal Structure and Charge-TransporL Properties of Hexacene", Nature Chemistry, Jun. 2012, vol. 4, No. 7, p. 574-p. 578.*
Mondal et al., "Revisiting the Stability of Hexacenes", Organic Letters, May 22, 2007, vol. 9, No. 13, p. 2505-p. 2508.*
"Office Action of Taiwan Counterpart Application", issued on Mar. 11, 2014, p. 1-p. 7.
Watanabe et al., "The Synthesis, Crystal Structure and Charge-Transport Properties of Hexacene", Nature Chemistry, Jun. 2012, vol. 4, No. 7, p. 574-p. 578.
Laudise et al., "Physical Vapor Growth of Organic Semiconductors", Journal of Crystal Growth, Dec. 16, 1997, vol. 187, p. 449-p. 454.

* cited by examiner

*Primary Examiner* — Charles Boyer
(74) *Attorney, Agent, or Firm* — Jianq Chyun IP Office

(57) ABSTRACT

A hexacene derivative is described, being expressed by formula (1):

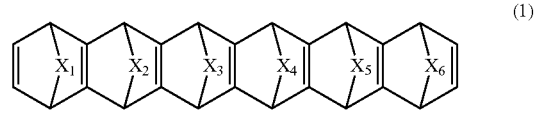

(1)

wherein $X_1$-$X_6$ denote the presence or absence of a carbonyl bridge [—C(=O)—], with a proviso that at least one of $X_1$-$X_6$ is a carbonyl bridge while any six-member ring absent of a carbonyl bridge is aromatic. A method for forming hexacene is also described, including: thermally treating the hexacene derivative to expel volatile units of CO from the hexacene derivative.

19 Claims, 4 Drawing Sheets

HEXACENE DERIVATIVE, METHOD FOR FORMING HEXACENE, METHOD FOR FORMING HEXACENE CRYSTAL, PROCESS FOR MAKING ORGANIC SEMICONDUCTOR DEVICE, AND ORGANIC SEMICONDUCTOR DEVICE

BACKGROUND OF THE INVENTION

1. Field of Invention

This invention relates to a hexacene derivative that can serve as a precursor of hexacene, a method for forming hexacene from the hexacene precursor, a method for forming a hexacene crystal from thus formed hexacene, a process for making an organic semiconductor device that utilizes the method for forming a hexacene crystal, and an organic semiconductor device made through the process.

2. Description of Related Art

Acenes are a class of aromatic hydrocarbons composed of linearly fused benzene rings. Functional acenes are of contemporary interests both in theoretical aspect and as a new type of organic materials. One of the most attractive features of acenes is their exceptionally narrow HOMO-LUMO band gap, which leads to the highest conductivity than any other kinds of organic compounds. The hole mobility in single crystals of acenes, measured in organic field-effect transistor (OFET) across gold electrodes on top of $SiO_2$, increases with the number of aromatic rings, e.g., anthracene ($\mu_{FET}$, 0.02 cm$^2$ V$^{-1}$ s$^{-1}$)<tetracene ($\mu_{FET}$, 0.4 cm$^2$ V$^{-1}$ s$^{-1}$)<pentacene ($\mu_{FET}$, 1.4 cm$^2$ V$^{-1}$ s$^{-1}$).

Although larger acenes have great potential in a wide range of applications, their utilities are limited severely by both the low solubility and low stability in solutions. Hexacene, for example, has been reported more than 70 years ago, yet its property has never been unambiguously described until recently. The reason was mainly due to its tedious synthesis and low solubility.

To increase the solubility, a series of peri-functionalized derivatives containing silylethynyl and organothio substituents have been synthesized. These types of derivatives, including heptacene and nonacene, have indeed showed higher stability and solubility in solutions. For non-substituted hexacene, a recent synthesis has been achieved through a photo-induced expulsion of CO molecules from a diketone precursor, while the product was collected by matrix isolation, as described in Mondal, R. et al., "Revisiting the stability of hexacenes", *Org. Lett.* 9, 2505-2508 (2007). Under room temperature in the polymer matrix, the product can be kept for more than 12 hours. However, hexacene crystals could not be obtained by this method.

A similar matrix isolation has also been conducted recently on the preparation of non-substituted nonacene. It has been established that the photo-expulsion of CO through diketone precursors proceeded through biradical intermediates. In the case of pentacene, the yield was only 74% ($\tau_T$=48.48±0.15 µs) from its diketone precursor.

SUMMARY OF THE INVENTION

Accordingly, this invention provides a hexacene derivative that can serve as a precursor of hexacene.

This invention also provides a method for forming hexacene from the hexacene precursor.

This invention further provides a method for forming a hexacene crystal from the hexacene formed with the above method.

This invention further provides a process for making an organic semiconductor device that utilizes the method for forming a hexacene crystal of this invention.

This invention further provides an organic semiconductor device made through the above process of this invention.

The hexacene derivative of this invention is expressed by formula (1):

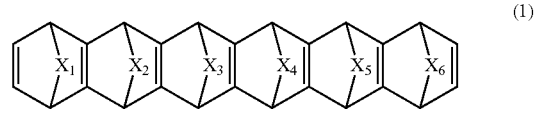

(1)

wherein $X_1$-$X_6$ denote the presence or absence of a carbonyl bridge [—C(=O)—], with a proviso that at least one of $X_1$-$X_6$ is a carbonyl bridge while any six-member ring absent of a carbonyl bridge is aromatic.

The method for forming hexacene of this invention includes thermally treating the above hexacene derivative to expel volatile units of CO therefrom.

The method for forming a hexacene crystal of this invention includes performing a sublimation-deposition process with the hexacene formed by the above method.

In an embodiment of this invention, the above sublimation-deposition process includes a physical vapor transport (PVT) process.

The process for making an organic semiconductor device of this invention includes: applying the above hexacene crystal formation method to form a hexacene crystal layer over a substrate for carrying the organic semiconductor device, wherein the hexacene crystal layer serves as an active layer of the organic semiconductor device.

By using the hexacene derivative of this invention as a precursor of hexacene, a highly efficient solid-state synthesis of hexacene is possible.

Moreover, by thermally degradation of the monoketone precursor of hexacene, biradical intermediates can be avoided to prevent oxygen trapping. In addition, when the reaction is conducted in the dark, the possibility of photo-induced oxidation and/or dimerization can be minimized. Pure hexacene thus prepared can be stored under ambient condition in the dark for more than 1 month.

Furthermore, platelet single crystals can be obtained by way of sublimation-deposition, such as physical vapor transport (PVT), from the above-prepared hexacene. X-ray diffraction analysis of the hexacene crystal obtained by way of PVT indicates that hexacene molecules are aligned in herringbone arrays, just like pentacene.

Moreover, the OFET device as an organic semiconductor device made with such formed single crystals of hexacene and the PVT process can display a hole mobility as high as 4.28 cm² V⁻¹ s⁻¹ with an on/off ratio of 1×10⁵ and a threshold voltage of 37 V. Accordingly, the hexacene crystal obtained with the method of this invention can have an excellent effect in organic semiconductor devices.

In order to make the aforementioned and other objects, features and advantages of this invention comprehensible, a preferred embodiment accompanied with figures is described in detail below.

BRIEF DESCRIPTION OF THE DRAWINGS

FIG. 4A shows the output characteristics, wherein D is the drain, S is the source, and inset shows a crystal across the electrodes, with a scale bar of 50 μm and W/L=1.10.

FIG. 4B shows the transfer characteristics recorded at $V_{DS}$=−80V (G is the gate).

FIG. 4C show the time-dependent decay of performance at ambient condition in a $N_2$-atmosphere.

FIG. 4D shows a current (J) vs. electric field (E) plot of a hexacene crystal across gold electrodes at ambient condition (the inset is an I-V plot at low voltage (−1 to 1 V).

DESCRIPTION OF EMBODIMENTS

Figure 1A:
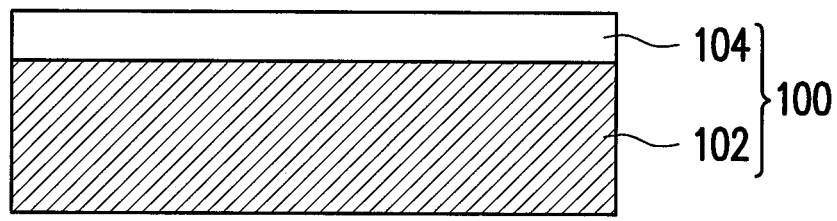
FIGS. 1A and 1B illustrate a process for making an organic semiconductor device according to an embodiment of this invention, wherein FIG. 1B also illustrate an organic semiconductor device according to the embodiment.

The following description is merely exemplary in nature and is not intended to limit the present disclosure, application, or uses. The oligoacene precursors provided herein are precursors for hexacene that has the following structure:

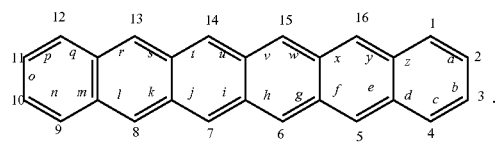

<Hexacene Derivative>

The hexacene derivative of this invention is expressed by formula (1):

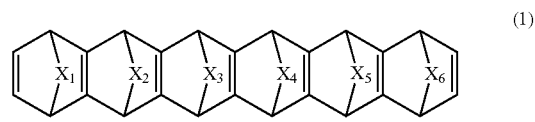

wherein $X_1$-$X_6$ denote the presence or absence of a carbonyl bridge [—C(═O)—], with a proviso that at least one of $X_1$-$X_6$ is a carbonyl bridge while any six-member ring absent of a carbonyl bridge is aromatic. For example, $X_1$, $X_2$ or $X_3$ is a carbonyl bridge while the six-member rings of the others of $X_1$-$X_6$ are aromatic, or $X_2$ and $X_4$ are carbonyl bridges while the six-member rings of the others of $X_1$ to $X_6$ are aromatic, or $X_2$ and $X_5$ are carbonyl bridges while the six-member rings of the others of $X_1$ to $X_6$ are aromatic. The hexacene derivative where $X_3$ is a carbonyl bridge and the six-member rings of the others of $X_1$-$X_6$ are aromatic, namely 6,15-oxomethylene-bridged hexacene, is illustrated below as a representative:

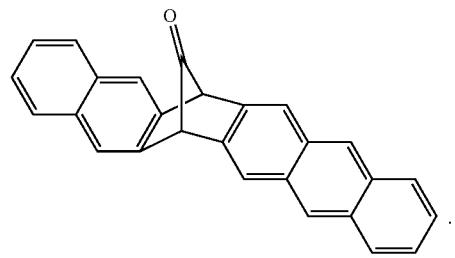 [SMILES: O=C1C2c3cc4ccccc4cc3C1c1cc3cc4ccccc4cc3cc12]

The hexacene derivative of formula (1) can be synthesized based on fusion of two or more compounds each having a single or multiple six-member rings, one or more of which have a substituted methylene bridge on a six-member ring thereof.

For example, the 6,15-oxomethylene-bridged hexacene corresponding to formula (1) with $X_3$ being a carbonyl bridge can be synthesized by the Scheme 1 below, wherein two anthracene derivatives each having three six-member rings are fused firstly, and one of which has a substituted methylene bridge on a six-member ring thereof. The hexacene derivative where $X_2$ is a carbonyl bridge and the six-member rings of the others of $X_1$-$X_6$ are aromatic can be synthesized starting from the Scheme 2 below. The hexacene derivative where $X_2$ and $X_4$ are carbonyl bridges and the six-member rings of the others of $X_1$-$X_6$ are aromatic can be synthesized by the Scheme 3 below, wherein a compound having three six-member rings and having a substituted methylene bridge on a six-member ring thereof, a compound having a single six-member ring, and a compound having two six-member rings and having a substituted methylene bridge on a six-member ring thereof are fused in sequence.

Scheme 1:
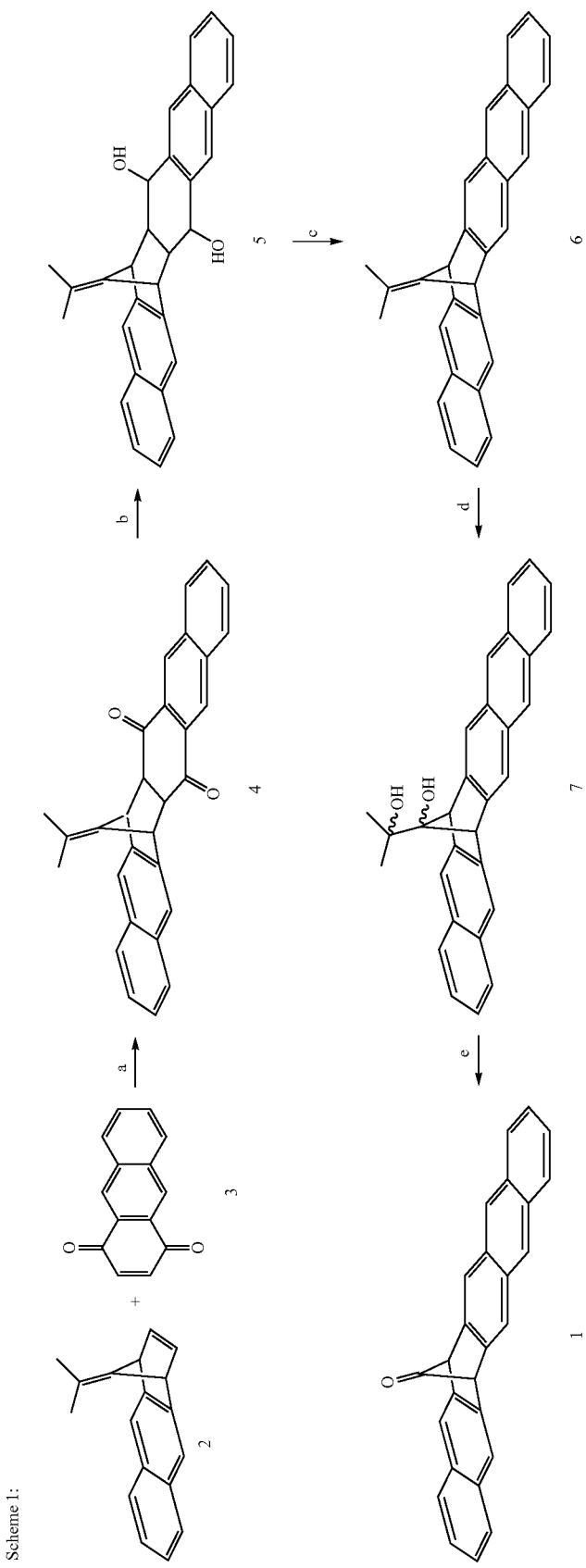
a: 3,6-bis(2-pyridyl)-tetrazine, toluene reflux, 59%; b: NaBH₄, THF, MeOH; c: POCl₃, NaI, pyridine, 54% (2 steps from 4); d: OsO₄, N-methylmorpholine N-oxide (NMO), acetone, H₂O; e: Pd(OAc)₂, benzene, 74% (2 steps from 6)

Scheme 2:

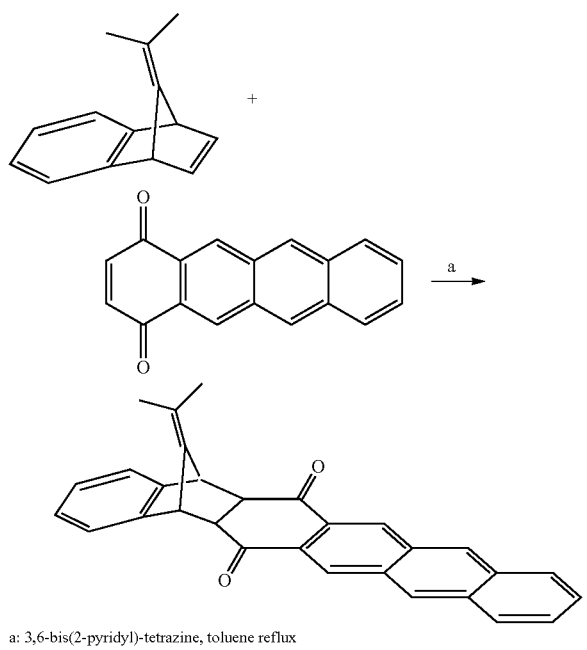

a: 3,6-bis(2-pyridyl)-tetrazine, toluene reflux

Scheme 3:

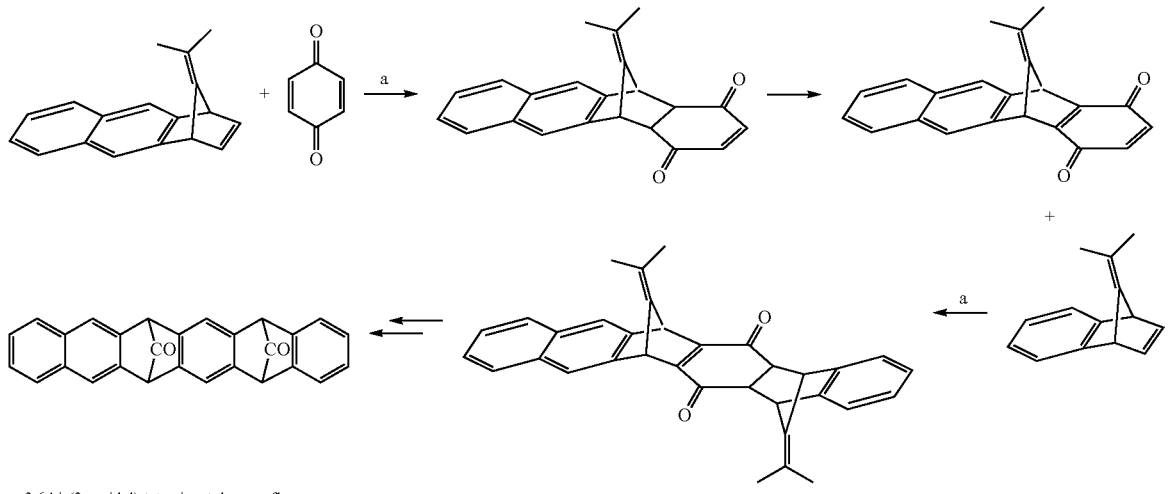

a: 3,6-bis(2-pyridyl)-tetrazine, toluene reflux

<Formation of Hexacene from the Hexacene Derivative>

The method for forming hexacene of this invention includes thermally treating the above hexacene derivative to expel volatile units of CO therefrom. The thermal treatment may be conducted at a temperature with the range of 180-200° C. The treatment time is usually from 2 min to 5 min, depending on the quantity of the hexacene derivative being treated. The thermal treatment can be conducted in a dark environment, so as to minimize the possibility of photo-induced oxidation and/or dimerization. In addition, wherein the hexacene derivative is usually thermal treated in a form of a powder.

<Formation of Hexacene Crystal from the Hexacene Formed as Above>

A method for forming a hexacene crystal of this invention includes: performing a sublimation-deposition process with the hexacene formed by the above method for forming hexacene. An example of the sublimation-deposition process is the physical vapor transport (PVT) process, as described in Laudise, R. A. et al. "Physical vapor growth of organic semiconductors", *J. Cryst. Growth*. 187, 449-454 (1998).

The process of utilizing PVT to form hexacene crystals from the hexacene powder obtained as above may include the following steps. The hexacene powder is transferred into a glass tube for PVT, and the tube is heated in an oven at 260-300° C., preferably with a flow of argon gas to prevent access of oxygen. Blue-green platelet crystals of hexacene can be collected at a proper temperature gradient zone inside the glass tube.

<Organic Semiconductor Device Having the Hexacene Crystal and its Fabrication>

Figure 1B:
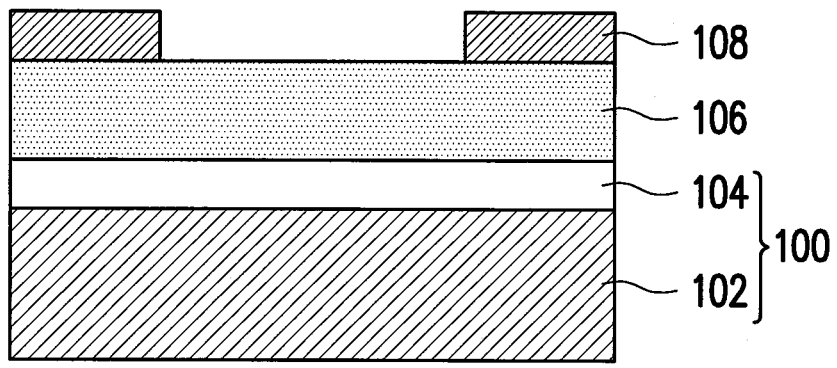

FIGS. 1A and 1B illustrate a process for making an organic semiconductor device according to an embodiment of this invention, wherein FIG. 1B also illustrate an organic semiconductor device according to the embodiment. The organic semiconductor device exemplified in this embodiment is an organic field-effect transistor (OFET).

Referring to FIG. 1A, a substrate 100 for the OFET is provided, which may include a gate conductive layer 102 and a gate dielectric layer 104 thereon. The gate conductive layer 102 may include single-crystal silicon. The gate dielectric layer 104 may include $SiO_2$. In addition, the $SiO_2$ layer may be coated with a self-assembled monolayer (SAM) of octyltrichlorosilane (OcTS), so as to improve the dielectric nature of the surface of the $SiO_2$ layer.

Referring to FIG. 1B, a sublimation-deposition process is applied to the substrate 100 with the hexacene powder obtained from thermal degradation of the hexacene precursor of this invention as a to-be-deposited material to form a hexacene crystal layer 106 on the gate dielectric layer 104. The hexacene crystal layer 106 serves as an active layer of the OFET. Then, source/drain (S/D) electrodes 108 are formed on the hexacene crystal layer 106, possibly by a deposition process through a shadow mask. The S/D electrodes 108 may include gold (Au), silver (Ag), copper (Cu) or aluminum (Al).

Accordingly, the OFET as an organic semiconductor device according to this embodiment includes a gate conductive layer 102, a gate dielectric layer 104 on the gate conductive layer 102, a hexacene crystal layer 106 formed through thermal degradation of the hexacene precursor of this invention and a subsequent sublimation-deposition process, and S/D electrodes 108 on the hexacene crystal layer 106.

Some examples are provided below to further explain this invention, which are however not intended to limit the scope of this invention.

EXAMPLES

Synthesis of Hexacene Derivative or Hexacene Precursor

The hexacene precursor (1) used in the examples of this invention is synthesized with the above-mentioned Scheme 1. The hexacene precursor 1 is soluble in common organic solvents, such as chloroform and THF, in a solubility of about 0.3 mg/mL, and the solid can be stored at 5° C. under room light for more than 6 months.

Also, the hexacene precursor 1 ($2.0 \times 10^{-4}$ M in THF) displayed the characteristic $^1A \rightarrow ^1L_a$ transitions of anthracene chromophore with vibronic progressions at 385 ($\log \in =3.81$), 365 ($\log \in =3.96$) and 347 nm ($\log \in =3.88$).

<Formation of Hexacene from the Hexacene Precursor>

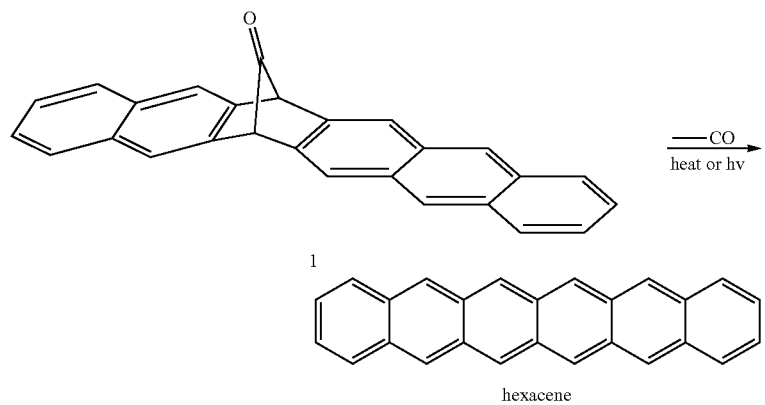

The conversion of the hexacene precursor 1 to hexacene was first attempted by using a photochemical method. When a THF solution was irradiated at 365±30 nm (12.5 mW/cm² UV under an oxygen-free condition), the absorption bands of the hexacene precursor 1 diminished along with the growth of new bands at 667, 611, and 557 nm (shoulder) corresponding to the vibronic progressions of π-π*transition of hexacene. However, these new bands persisted only briefly and then disappeared, probably due to dimerization.

Figure 2A:
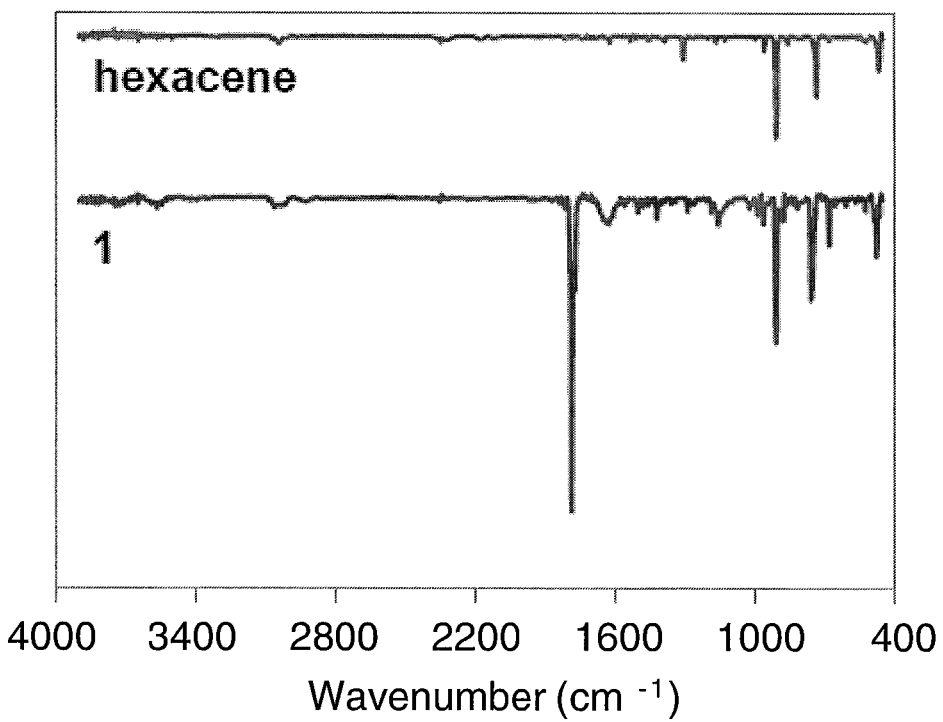
FIGS. 2A-2C respectively show the change in the IR spectrum, the TGA analysis result, and the change in the CP-MAS NMR spectrum in the process of thermally degrading the hexacene precursor of this invention to form hexacene.

On the other hand, thermal conversion was independently attempted by heating the hexacene precursor 1 in the solid form to approximately 180° C. in a $N_2$-atmosphere. Under this condition, the color changed rapidly from white to blue-green. During the thermal transformation, the characteristic carbonyl peak of 1 at 1784 cm$^{-1}$ diminished, as shown in the IR spectrum in FIG. 2A. The high-resolution MALDI-MS spectrum indicated a molecular ion signal at m/z 329.1341 (MH$^+$, calcd 329.1330, error=3.0 ppm), corresponding to hexacene.

Figure 2B:
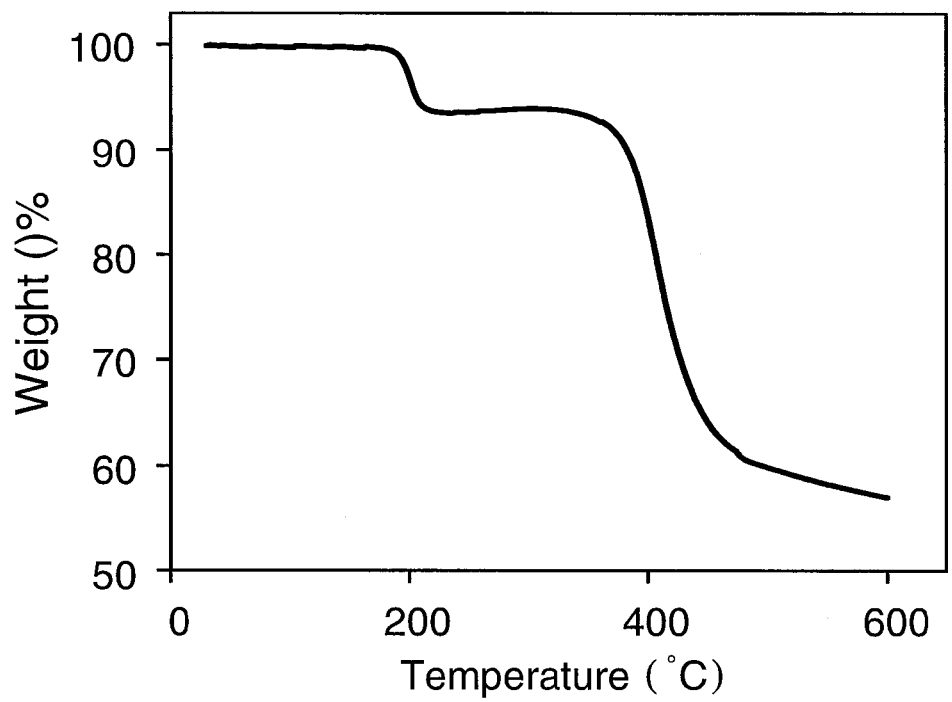

Moreover, a thermal gravimetric analysis (TGA) of the hexacene precursor 1 was carried out with a scan rate of 10° C./min under a $N_2$-flow, and the result is shown in FIG. 2B. A weight loss of 6.6% (calcd 7.9%) happened at ca. 180° C., corresponding to the formation of hexacene through a CO-expulsion. The sample then stayed stable over a wide temperature range until ca. 330° C., at which another weight loss appeared due to vaporization.

Figure 2C:
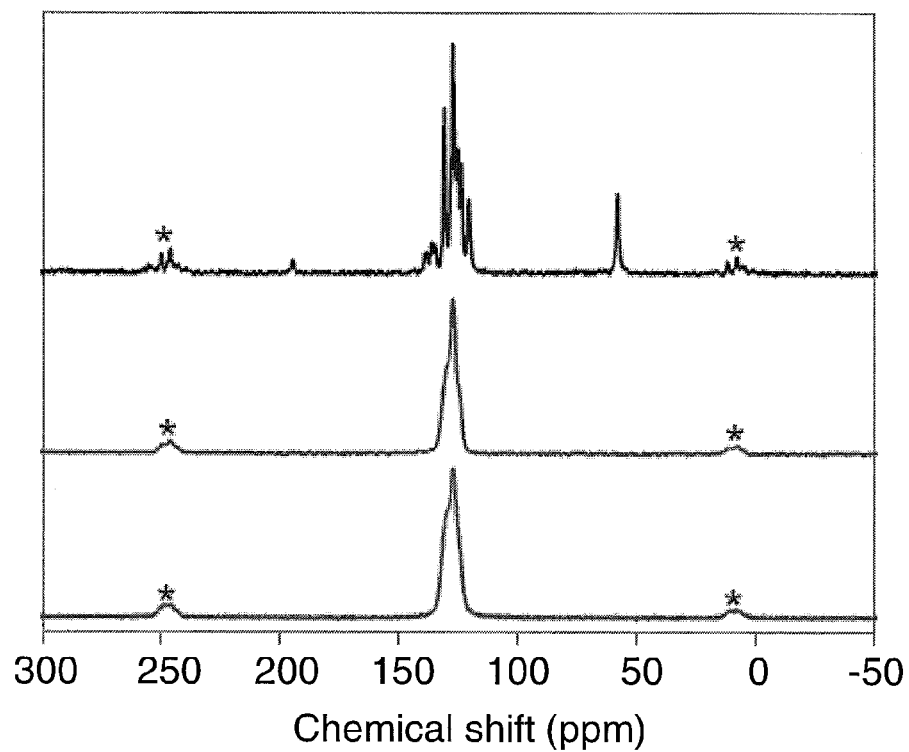

The formed hexacene was also examined by solid-state cross-polarization magic angle spinning (CP-MAS) NMR, and the result is shown in FIG. 2C, wherein the top spectrum is of the hexacene precursor 1, the middle one is of the hexacene produced by heating the hexacene precursor 1 at 180° C. under an $N_2$-atmosphere, the bottom one is of the hexacene left at ambient condition in the dark for 30 days, and the asterisks denote spinning sidebands.

The spectrum of the hexacene precursor 1 showed three absorption bands at δ 57.7 (bridgehead), 120-139 (aromatic), and 194.7 (carbonyl) ppm. After the thermal conversion, the bridgehead and carbonyl peaks faded away and left behind only the aromatic ones at 121-134 ppm. The absence of any other signals in the spectrum indicated that the transformation had proceeded cleanly. A simulated spectrum calculated by the density function theory (DFT) B3LYP/6–311+G(2d,p)// M06/6–31G(d) matched well with the experimental one.

After being exposed to air at room temperature for 24 h in the dark, the hexacene gave virtually the same CP-MAS NMR spectrum (see the bottom one), thus indicating the high stability of hexacene under an ambient condition.

Further evidence on its high stability was provided by the solid state absorption spectra. A THF solution of the hexacene precursor 1 was spin-casted on a quartz plate (transparency>98% at 380 nm wavelength) into a 200 nm thick film, which was converted to hexacene by heating at 180° C. under a $N_2$-atmosphere. The film of the hexacene precursor 1 before heating displayed the characteristic feature of anthracene at 403 nm (3.08 eV). After heating, the band disappeared along with the growth of new peaks at 840 (1.48 eV), 765 (1.62 eV), 708 (1.75 eV), and 654 nm (1.90 eV). The low energy peaks were red-shifted with respect to those in a THF solution at 667 nm (1.86 eV), and can be rationalized by the effect of Davydov splitting. The peaks at 840 (1.48 eV) and 765 nm (1.62 eV) were assigned to Davydov doublet of 0-0 band, and those at 708 (1.75 eV) and 654 nm (1.90 eV) were Davydov doublet of 0-1 band. The hexacene film was stable for more than one month, when it was left in air at room temperature in the dark, as indicated by both the CP-MAS NMR spectra (the bottom spectrum in FIG. 2C) and the absorption spectra.

In an earlier report, it has been shown that hexacene in a polymethyl methacrylate (PMMA) matrix reacted gradually with dioxygen, which diffused slowly into the matrix, under the irradiation of a UV-LED array (395±25 nm). For comparison, the photochemical stability of a hexacene thin-film was investigated by shining with UV light at 365 nm (±30 nm using a 12.5 mW/cm² black light UV lamp, >400 nm filtered) in air. The absorption intensity of hexacene decreased gradually with the increase of a new band at ca. 430 nm. In the mean time, a new signal was observed in high-resolution MALDI-MS spectrum, which corresponded to an endoperoxide adduct (m/z 361.1238 (MH⁺), calcd 361.1228, error=2.8 ppm).

These results indicated that hexacene underwent a slow photochemical oxidation in the presence of air. A time-dependent measurement on the intensity of 840 nm band revealed that the amount of photo-oxidation increased steadily at the early stage, i.e., during 0-120 min, but slowed down substantially after 300 min. It indicated that the air oxidation proceeded mainly on the surface of the solids, as time went by it became more difficult for oxygen to penetrate into the interior of the solids which were shielded by the surface substances. The photo-ionization energy of hexacene thin-film was measured by photoemission yield spectroscopy (AC-2 Riken), and it was found that the HOMO level of hexacene (−4.96 eV) was higher than that of pentacene (−5.14 eV). The LUMO level of a thin film (−3.56 eV) was deduced by subtracting the HOMO from the edge of absorption band (889 nm, 1.40 eV).

The ultimate structural proof was the single crystal structure by X-ray diffraction analysis. Pure hexacene was obtained by using the physical vapor transport (PVT) method. A sample of the precursor 1 was heated at 180° C. in an $N_2$-atmosphere to give a sizable amount of pure hexacene. It was then transferred into a glass tube for PVT, and the tube was heated in an oven at 260-300° C. with a flow of argon gas in a flow rate of 20-40 mL/min. Blue-green platelet crystals were collected at a proper temperature gradient zone inside the glass tube.

Figure 3:
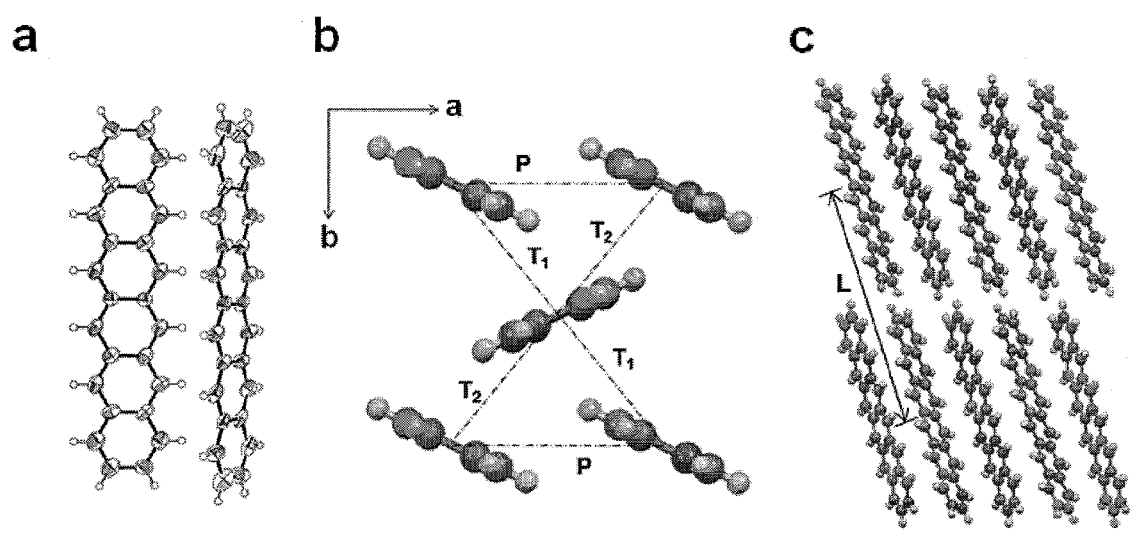
FIG. 3 illustrates the single crystal structure of the hexacene crystal obtained with the method of this invention, which was investigated by X-ray diffraction, including a) an ORTEP drawing of two adjacent hexacene molecules, b) the layer arrangement of hexacene molecules on the ab plane, and c) arrays of hexacene along the a axis, wherein the distances used for the computation of transfer integrals are denoted as $T_1$ and $T_2$ for transverses, P for parallel, and L for longitudinal.

A single crystal was picked up and subjected to an X-ray diffraction analysis. Crystal parameters were collected at −150° C. in the dark. The crystal belongs to the triclinic space group P-1, with a=6.292, b=7.673, c=16.424 Å, α=98.66°, β=91.16° and γ=95.71°. As shown in FIG. 3, the molecules are shown to be packed in herringbone arrays, quite analogous to pentacene. The result was consistent with the expectations (triclinic crystal of space group P-1), with only a slight variation in the unit-cell dimension (a=7.9, b=6.1, c=18.4 Å, α=102.7°, β=112.3°, γ=83.6°. The herringbone packing motif is believed to be responsible for the high stability of solid state hexacene.

As compared to the hexacene derivatives with silylethynyl substituents, e.g., the tri-isobutylsilylethynylhexacene (TIBS-hexacene), the non-substituted hexacene in the crystal exhibited a very slow rate of dimerization. In the crystal of TIBS-hexacene the adjacent molecules are arranged in a shifted face-to-face π-stacking motif, a geometry which is more likely to dimerize.

In the herringbone packing of non-substituted hexacene, the adjacent molecules are stacked in an edge-to-face manner, which is not suitable for dimerization. It is well known that the electronic property of acenes depends heavily on their molecular packing patterns. Based on the crystal data, the transfer integrals of naphthalene, anthracene, tetracene, pentacene, and hexacene were compared. The results showed that hexacene has a much smaller reorganization energy ($\lambda^+$) and a higher electronic coupling ($t^+$) along both $T_1$ and $T_2$ directions (FIG. 3), thus a significantly higher hole mobility ($\mu^+$) than other acenes was expected (Table 1). The hole mobility can be fitted well into an equation related to the number of aromatic rings, i.e., $ax^b$ (x=2-6). The calculations also suggest that the hole mobility of hexacene is most efficient along the ab plane.

TABLE 1

Calculated hole transporting property.

| Comp. | HOMO[a] (eV) | $\lambda^{+a}$ (meV) | R (Å), $t^+$ (meV)[b] | | | | $\mu^{+c}$ (cm²V⁻¹s⁻¹) |
|---|---|---|---|---|---|---|---|
| | | | $T_1$ | $T_2$ | P | L | |
| Naphthalene[d] | −5.80 | 183 | 5.01, 8 | 5.01, 8 | 5.93, 36 | 8.64, 0 | 0.0511 |
| Anthracene[e] | −5.24 | 138 | 5.22, 19 | 5.22, 19 | 6.01, 42 | 11.12, 0 | 0.158 |
| Tetracene[f] | −4.87 | 113 | 4.77, 70 | 5.13, 22 | 6.06, 37 | 13.44, 1 | 0.470 |
| Pentacene[g] | −4.61 | 95 | 4.76, 79 | 5.21, 45 | 6.27, 31 | 16.11, 1 | 0.832 |
| Hexacene | −4.42 | 79 | 4.72, 88 | 5.22, 60 | 6.31, 37 | 18.61, 1 | 1.461 |

[a]B3LYP/6-31G(d,p) level,
[b]PW91/DZ2P level calculated at 300K.
$t^+$ is given as absolute value.
[c]averaged value along the four directions ($T_1$, $T_2$, P, and L) under consideration.
[d]ref31.
[e]ref32.
[f]ref33.
[g]ref34.

<Fabrication of OFET>

Figure 4A:
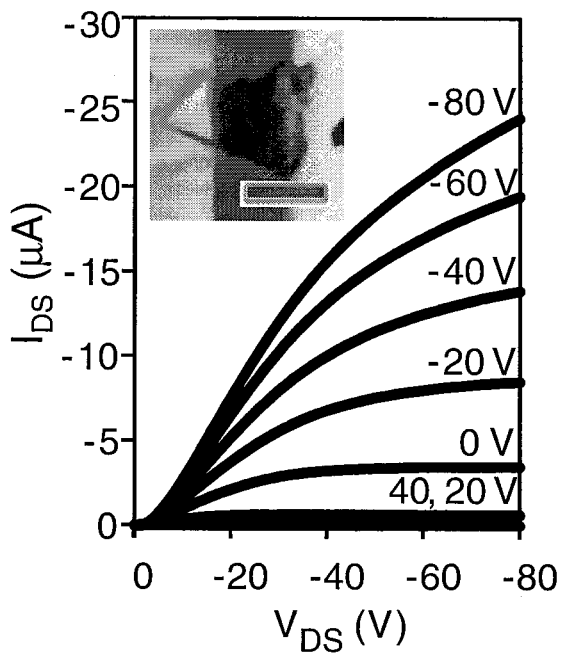
FIGS. 4A-4D show the conductivity characteristics of a single-crystal hexacene OFET.
Figure 4B:
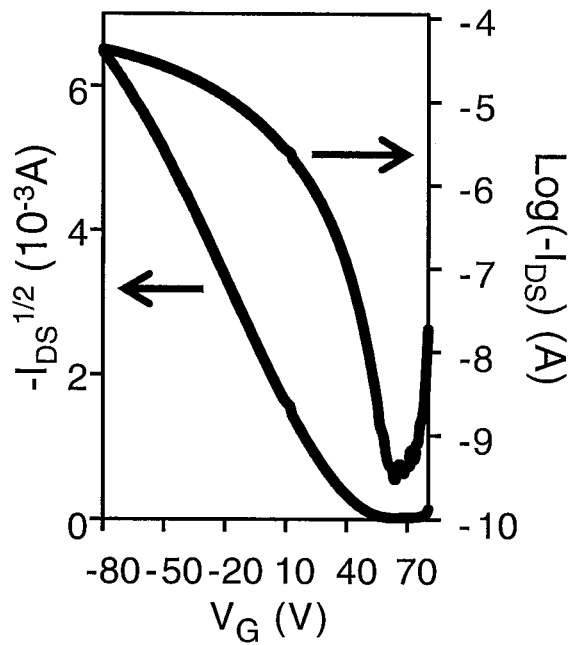

Field effect transistors were attempted by using the single crystals of hexacene. The crystals were grown on a $SiO_2$/Si substrate, which was coated with a self-assembled monolayer (SAM) of octyltrichlorosilane (OcTS) and placed inside the PVT tube. After the crystal growth, gold electrodes of source and drain were thermally deposited on top of the substrate through a shadow mask. The averaged performance of 14 independent devices was 0.88 cm² V⁻¹ s⁻¹, with a threshold at 34 V and an on/off ratio of 10⁴-10⁶. Among them the best mobility was 4.28 cm² V⁻¹ s⁻¹ with an on/off ratio of 1×10⁵ and threshold 37 V, as shown in FIGS. 4A-4B.

Figure 4C:
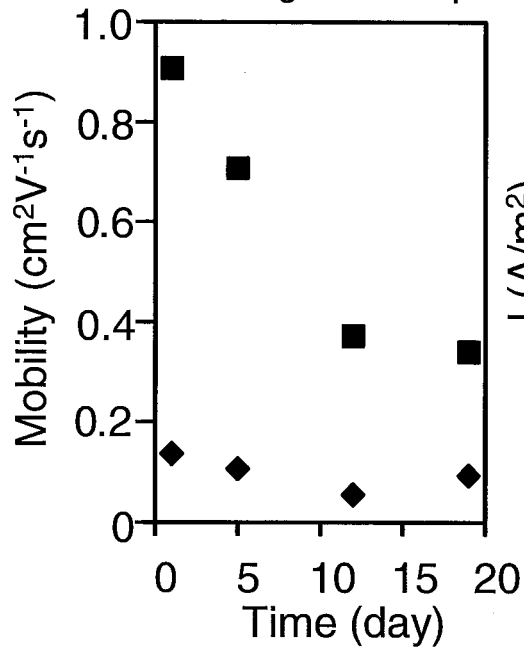

These FET devices without encapsulation could function effectively for more than 19 days. During the time a device was kept at ambient environment under room light, the mobility reduced gradually from 0.906 cm² V⁻¹ s⁻¹ to 0.339 cm²V⁻¹ s⁻¹ (67% decay). When it was stored in a nitrogen atmosphere, the mobility reduced from 0.135 cm²V⁻¹ s⁻¹ to 0.092 cm²V⁻¹ s⁻¹ (32% decay), as shown in FIG. 4C. The decay was believed to be caused by air oxidation on the surface of the crystal.

Further, it is well known that the performance of transistors depends significantly on the nature of gate dielectric. The hole mobility of pentacene has been reported to be in the proximity of 0.1-1.4 cm$^2$ V$^{-1}$ s$^{-1}$ for a single crystal, about 3.4 cm$^2$ V$^{-1}$ s$^{-1}$ for a thin-film on top of SiO$_2$, and 0.25-15 cm$^2$ V$^{-1}$ s$^{-1}$ in the presence of other type of surface treatments. In this study the hole mobility of a single-crystal hexacene FET was better than the best of pentacene FETs on top of SiO$_2$ with OcTS SAM treatment. For comparison, a single crystal of pentacene fabricated in an identical manner to that of hexacene showed a hole mobility 1.2 cm$^2$ V$^{-1}$ s$^{-1}$ with an on/off ratio of 3×10$^6$ and a threshold at −7 V.

Figure 4D:
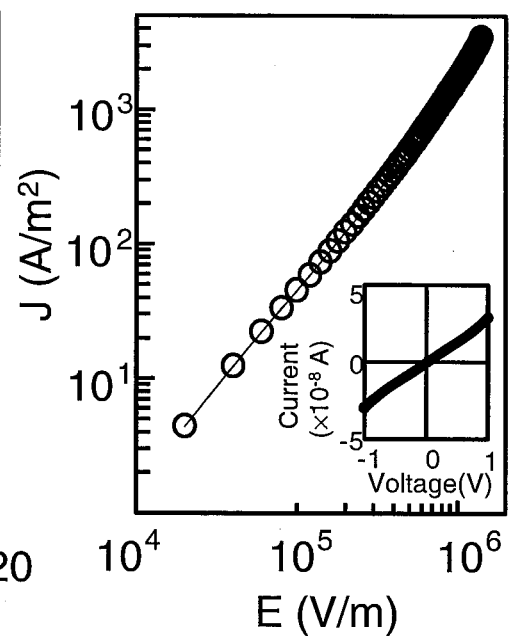

The conductivity of crystalline hexacene was also measured under a gate-free condition. Deduced from the J-E plot, as shown in FIG. 4D, the conductivity of crystalline hexacene was estimated to be 2.21×10$^{-4}$ Sm$^{-1}$ ($V_{sd}$=1 V), which was slightly higher than that of pentacene (2.13×10$^{-5}$ Sm$^{-1}$ to 2.13×10$^{-6}$ Sm$^{-1}$) (FIG. 4D).

Accordingly, with this invention, the nature of pure hexacene is successfully characterized for the first time. It can be concluded that solid state hexacene is thermally stable up to about 300° C. in the dark, but highly vulnerable in solutions under light.

Furthermore, platelet single crystals can be obtained by way of sublimation-deposition, such as physical vapor transport (PVT), from the above-prepared hexacene. X-ray diffraction analysis of the hexacene crystal obtained by way of PVT indicates that hexacene molecules are aligned in herringbone arrays, just like pentacene.

Moreover, the OFET device as an organic semiconductor device made with such formed single crystals of hexacene and the PVT process can display a hole mobility as high as 4.28 cm$^2$ V$^{-1}$ s$^{-1}$ with an on/off ratio of 1×10$^5$ and a threshold voltage of 37 V. This is an excellent result as compared to the prior-art OFET devices based on smaller acenes.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:

1. A hexacene derivative, being expressed by formula (1):

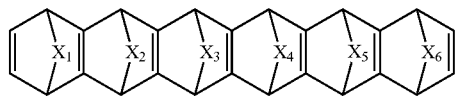

(1)

wherein each of $X_1$ to $X_6$ denotes presence or absence of one carbonyl bridge expressed as "—C(═O)—", with a proviso that at least one of $X_1$ to $X_6$ is the one carbonyl bridge while any six-member ring absent of the one carbonyl bridge is aromatic.

2. The hexacene derivative of claim 1, wherein $X_2$ or $X_3$ is the one carbonyl bridge while the six-member rings of the others of $X_1$ to $X_6$ are aromatic.

3. The hexacene derivative of claim 1, wherein $X_2$ and $X_4$ are carbonyl bridges while the six-member rings of the others of $X_1$ to $X_6$ are aromatic.

4. The hexacene derivative of claim 1, wherein $X_2$ and $X_5$ are carbonyl bridges while the six-member rings of the others of $X_1$ to $X_6$ are aromatic.

5. A method for forming hexacene, comprising: thermally treating the hexacene derivative of claim 1 to expel volatile units of CO from the hexacene derivative.

6. The method of claim 5, which is conducted in a dark environment.

7. The method of claim 5, wherein the hexacene derivative is thermally treated at a temperature with the range of 180-200° C.

8. The method of claim 5, wherein the hexacene derivative is thermally treated in a form of a powder.

9. A method for forming a hexacene crystal, comprising: performing a sublimation-deposition process with the hexacene formed by the method of claim 5.

10. The method of claim 9, wherein the sublimation-deposition process comprises a physical vapor transport (PVT) process.

11. A process for making an organic semiconductor device, comprising: applying the method of claim 10 to form a hexacene crystal layer over a substrate for the organic semiconductor device, wherein the hexacene crystal serves as an active layer of the organic semiconductor device.

12. The process of claim 11, wherein the organic semiconductor device comprises an organic field-effect transistor (OFET).

13. The process of claim 12, wherein the substrate comprises a gate conductive layer and a gate dielectric layer over the gate conductive layer.

14. The process of claim 13, further comprising: forming source/drain (S/D) electrodes on the hexacene crystal layer.

15. An organic semiconductor device, comprising a hexacene crystal layer serving as an active layer thereof.

16. The organic semiconductor device of claim 15, which is an organic field-effect transistor (OFET).

17. The organic semiconductor device of claim 15, wherein the hexacene crystal layer is formed through steps comprising:

thermally treating a hexacene derivative to expel volatile units of CO from the hexacene derivative to form hexacene, wherein the hexacene derivative is expressed by formula (1):

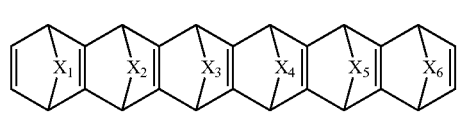

(1)

wherein each of $X_1$-$X_6$ denotes the presence or absence of one carbonyl bridge expressed as "—C(═O)—", with a proviso that at least one of $X_1$-$X_6$ is the one carbonyl bridge while any six-member ring absent of the one carbonyl bridge is aromatic; and performing a physical vapor transport (PVT) process with the formed hexacene as a to-be-deposited material and the gate dielectric layer as a target.

18. The organic semiconductor device of claim 17, which is an organic field-effect transistor (OFET).

19. The organic semiconductor device of claim 18, wherein the OFET comprises:

a gate conductive layer;
a gate dielectric layer over the gate conductive layer;
the hexacene crystal over the gate dielectric layer; and
source/drain electrodes on the hexacene crystal.

* * * * *